United States Patent [19]

Jackson, Jr. et al.

[11] 3,986,935
[45] Oct. 19, 1976

[54] BIOLOGICAL CHAMBER APPARATUS

[75] Inventors: Richard Land Jackson, Jr., Elkhart, Ind.; John E. Martin, Jr., Atlanta, Ga.

[73] Assignee: Miles Laboratories, Inc., Elkhart, Ind.

[22] Filed: Aug. 7, 1975

[21] Appl. No.: 602,686

Related U.S. Application Data

[63] Continuation-in-part of Ser. No. 451,845, March 18, 1974, abandoned.

[52] U.S. Cl. .............................. 195/142; 195/139
[51] Int. Cl.² ........................................ C12B 1/00
[58] Field of Search ..................... 195/139, 142, 127

[56] References Cited
UNITED STATES PATENTS

| | | | |
|---|---|---|---|
| 3,165,450 | 1/1965 | Scheidt .............................. | 195/139 |
| 3,234,107 | 2/1966 | Kaufman et al. .................. | 195/139 |
| 3,272,719 | 9/1966 | Avakian ............................. | 195/139 |
| 3,660,243 | 5/1972 | Young ................................ | 195/139 |
| 3,677,904 | 7/1972 | Fitzgerald ......................... | 195/139 |

*Primary Examiner*—Alvin E. Tanenholtz
*Attorney, Agent, or Firm*—Louis E. Davidson

[57] ABSTRACT

Apparatus suitable for growth of microorganisms having a tray member with an open top and a closure member capable of being removably placed over the open top of the tray member. The tray member defines a main chamber therewithin and has wall means defining a separate open-topped chamber located within the main chamber, said wall means having an upper edge surface which is substantially coplanar with the open top of the tray member. At least one slot in the wall means provides communication between this separate chamber and the main chamber when the closure member is in place on the tray. When the apparatus is used, a suitable microbiological growth medium is placed in the main chamber and a gas-generating composition is placed in the separate chamber before the closure member is placed on the tray. Thereafter when the closure member is in place, gas from said composition can flow from the separate chamber into the main chamber to provide the desired atmosphere in said main chamber. Liquid within the separate chamber which may be introduced directly or may be condensate resulting from a humid atmosphere associated with the use of this apparatus or resulting from the reaction of the gas-generating composition is substantially retained therein when the cover is in place by what is believed to be a capillary-like attraction between the liquid, the upper edge surfaces of the separate chamber, the closure member and the surfaces of the slots.

12 Claims, 3 Drawing Figures

BIOLOGICAL CHAMBER APPARATUS

CROSS-REFERENCE TO RELATED APPLICATION

This application is a Continuation-in-Part of U.S. application Ser. No. 451,845 filed March 18, 1974, and now abandoned.

BACKGROUND AND PRIOR ART

Microorganisms are generally grown in covered tray-like receptacles, such as petri dishes. A growth medium, such as agar containing suitable nutrients, is placed in the tray, the culture of microorganisms is placed on the growth medium, a cover is placed over the tray and the covered tray is subjected to temperature conditions suitable for microorganism growth. If the atmospheric composition under which the microorganism grows is critical, the covered tray is usually placed in a chamber having a controlled atmosphere as well as temperature. In this case, suitable apparatus modifications are employed to enable the controlled atmosphere to easily enter the covered tray and contact the microorganism.

There is a need in the microbiological field for a biological chamber apparatus in which a controlled atmosphere can be generated.

SUMMARY OF THE INVENTION

In accordance with the present invention, biological chamber apparatus suitable for growth therein of microorganisms is provided comprising in combination (1) an open-topped tray member having a bottom wall and sidewalls extending upwardly therefrom to define a main chamber therewithin, and (2) a closure member capable of being removably placed over the open top of said tray member, said tray member having wall means defining a separate open topped chamber within the main chamber of said tray member extending to adjacent the plane of the open top thereof. At least one slot in the wall means provides communication between the separate chamber and the main chamber when said closure member is in place on the tray member.

DESCRIPTION OF THE INVENTION

Figure 1:
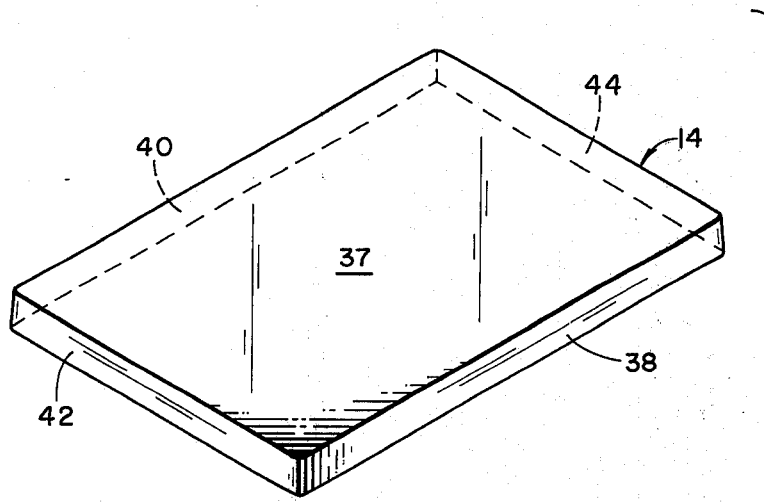
FIG. 1 is an exploded perspective view of one embodiment of the present invention.
Figure 1:
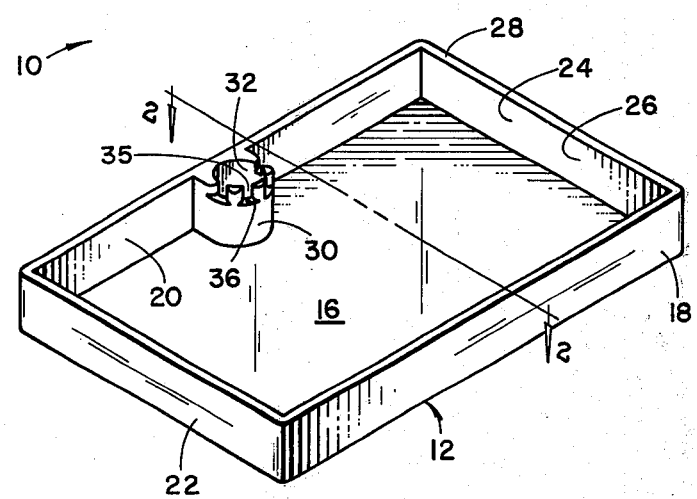
Figure 2:
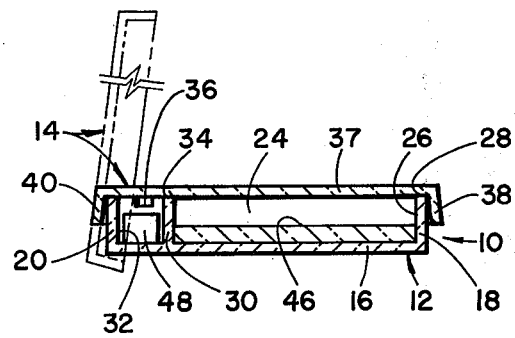
FIG. 2 is a cross-sectional view of the unexploded form of the apparatus of FIG. 1 taken along line 2—2 of FIG. 1 and showing a growth medium and a gas-generating tablet in place.

Referring to FIGS. 1 and 2, the apparatus 10 of the present invention comprises an open-topped tray member 12 and a closure member 14 capable of removably telescopically fitting over tray member 12 as shown in FIG. 2.

Tray member 12 has a planar bottom wall 16, longitudinal parallel planar sidewalls 18 and 20 and transverse parallel planar sidewalls 22 and 24 extending upwardly from bottom wall 16 to form a main chamber 26. The upper edges of sidewalls 18, 20, 22 and 24 form a continuous planar upper edge surface 28 of tray member 12. An additional wall means 30 which is generally U-shaped in plan view extends inwardly from sidewall 20 and upwardly from bottom wall 16, terminating in an upper edge surface 34 which is coplanar with surface 28. Wall means 30 forms a separate generally cylindrical open-topped chamber 32 within the main chamber 26 of tray member 12. Wall means 30 should not extend above the upper edge surface 28. At least one and preferably a plurality of slots 35 are formed in the upper end of wall means 30, each slot 35 extending downwardly to a lower end 36 which is spaced a predetermined distance from bottom wall 16. Slots 35 provide communication between chamber 32 and chamber 26 when closure member 14 is in place on tray member 12.

In the illustrated preferred embodiment, the generally cylindrical separate chamber 32 has an inner diameter at upper edge surface 34 of about 0.3 inch, the centerlines of the four slots 35 are at 45° angles one from the other about the axis of the separate chamber. At the inner surface of wall means 30 the slots 35 are about 0.05 inch wide and about 0.055 inch deep, and the merlons therebetween are about 0.06 inch wide. As shown in the drawing, the slots 35 flare outwardly toward the main chamber 26, giving the merlons therebetween a generally semicircular shape in plan view. Wall means 30 is about 0.04 inch thick. The tray member has internal dimensions of about 3 by 2 by 0.36 inches and the closure member has a telescopic fit thereover as shown.

Closure member 14 has a planar top wall 37, longitudinal generally parallel planar sidewalls 38 and 40 and transverse generally parallel planar sidewalls 42 and 44 depending therefrom. Closure member 14 is capable of removably telescopically fitting over the open end 28 of tray member 12 as shown in cross-section in FIG. 2. When closure member 14 is in this position, the upper edge surface 34 of wall means 30 and the top wall 37 of closure member 14 are in face-to-face contact and communication between the separate chamber 32 and the main chamber 26 of tray 12 is provided by slots 35.

In the use of the apparatus of the present invention, a growth medium 46, such as agar containing nutrients, is poured or otherwise placed in overlaying and adhering relation to the bottom of tray 12 outside of wall means 30 such that the exposed surface thereof is spaced below the lower ends 36 of slots 35. A microorganism to be grown is then applied to the exposed surface of the growth medium 46. A tablet 48 or other convenient form of a gas-generating composition is then placed in chamber 32 through the open top thereof. Closure member 14 is then placed on top of tray member 12 in the position shown in solid lines in FIG. 2, and the apparatus is subjected to an incubating temperature.

If a carbon dioxide atmosphere, for example, is desired in the main chamber 26, tablet 48 can be composed principally of citric acid and sodium bicarbonate, for example. Moisture from growth medium 46, upon contact with the tablet 48, causes a reaction between the citric acid and sodium bicarbonate to proceed, and generation of carbon dioxide gas and water results. This gas fills the chamber 32 and then flows into and fills the main chamber 26 above growth medium 46. It is understood that water or other activator could also be added directly to the gas-generating composition in chamber 32 if desired. However, for prolonged maintenance of the gaseous atmosphere within chamber 26, it is preferred that water in vapor form only contact tablet 48, and to this end wall means 30 prevents any direct contact of tablet 48 with growth medium 46. Further, it is essential that particles of the gas-generating composition do not come in contact with the growth medium.

When the apparatus described herein is used for growth of microorganisms, condensate from the humid atmosphere and/or water from the reaction of the gas-generating composition which forms in separate chamber 32 is retained within or on wall means 30 by what is believed to be capillary-like attraction between such liquid water and certain surface portions of said wall means and closure member 14. Such water is retained primarily between and along the upper edge surface 34 and the surface portion of closure member 14 face to face therewith, and extends as a liquid film across slots 35 along the adjacent surface portion of closure member 14. To a lesser extent, such water is retained along the surface of slots 35. Substantially all loose particulate matter from the gas-generating composition is entrapped in said water which effectively prevents contamination of the growth medium thereby.

Water could also be added to growth medium 46 in the event the growth medium material is supplied in a dehydrated form. It is also understood that other carbon dioxide-generating compositions could be employed as well as other compositions which can generate other desired gaseous atmospheres.

Figure 3:
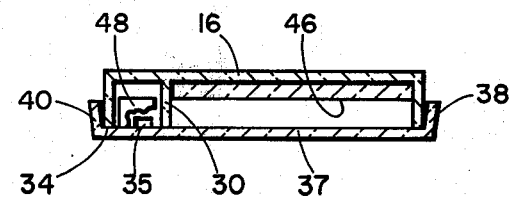
FIG. 3 is a cross-sectional view, similar to FIG. 2, showing the apparatus of the invention in inverted position.

By virtue of the described structure of the apparatus of the present invention, when closure member 14 is in place as shown in FIG. 2, the gas-generating composition is retained in the separate chamber 32 and out of contact with the growth medium layer in chamber 26, even when the apparatus is inverted as shown in FIG. 3 during incubation, storage or transporation, for example.

In order to minimize loss of desired atmosphere during the growth of the microorganism in the main chamber 26, it may be desirable to place the entire apparatus 10 in a further container such as a sealable organoplastic bag (not shown). The use of this overall bag is not a part of the present invention.

The above description relates to apparatus wherein the separate chamber 32 is located midway along one longitudinal sidewall of the tray members 12. It is understood that the present invention also includes apparatus wherein the separate chamber is located at other places within the main chamber. The significant features necessary are that the separate chamber have an open end through which the gas-generating composition is introduced and that there be at least one slot in the wall of such separate chamber providing communication with the main chamber when the closure member is in place on the tray member. The slot has a dimension such that in use of the apparatus as described, a liquid film extends along the inner surface of the closure member and across the slot, as well as on the surfaces of the slot and at the mating surface portions of the closure member and wall means 30, so that liquid within the separate chamber 32 is substantially retained therein.

The apparatus of the present invention need not be limited to rectangular shaped trays and closure members. A circular configuration, for example, can be used if desired.

Apparatus of the present invention is adapted for rapid use by technicians in screening for possible disease. In such use, it is desirable that the technician use one hand to open and close the biological chamber apparatus and the other hand to collect samples and apply them to the growth medium layer. In the preferred rectangular configuration shown in the drawing the sidewalls 38, 40, 42 and 44, and particularly the longitudinal sidewalls 38 and 40, of closure member 14, slant outward slightly as shown. It is preferred to have the cover sidewalls slant outwardly at an obtuse angle of at least about 91° from the plane of the top wall 37 of the cover to accomplish the purposes of the invention.

When such apparatus is employed, the technician can hold the tray member in one hand and move the closure member 14 with fingers of the same hand to the open position thereof shown in dot and dash lines in FIG. 2. This is best accomplished by lifting the longitudinal side of closure member 14 at sidewall 38 thereof away from the corresponding longitudinal side of tray member 12, while at the same time pivoting or rocking closure member 14 about the upper edge of the longitudinal sidewall 20 at the opposite side of tray 12. During such opening movement portions of the transverse sidewalls 42 and 44 of closure member 14 adjacent sidewall 40 thereof remain in overlapping relation with portions of the transverse sidewalls 22 and 24, respectively, of tray 12 adjacent the sidewall 20 thereof, thus facilitating manual control of both the closure member and tray during such manipulation. The same fingers can then close the chamber when desired by rocking closure member 14 in the reverse direction to its closed position shown in solid lines in FIG. 2. This frees the other hand of the technician for handling microorganism samples.

The various elements of this apparatus are conveniently formed from organoplastics. While it is not necessary, it is preferred that the closure member 14 be transparent so that microorganism growth in the main chamber can be observed.

The apparatus of the present invention has the technical and commercial advantages of convenience and simplicity of operation. It is an advance in the art of biological chamber apparatus.

What is claimed is:

1. A biological chamber apparatus comprising in combination an open-topped tray member having a generally planar bottom wall and having sidewall means extending upwardly from said bottom wall to define a main chamber therewith, said sidewall means terminating in a continuous planar upper edge surface, wall means defining a separate open-topped chamber within said main chamber, said wall means terminating in an upper edge surface substantially coplanar with said upper edge surface of said sidewall means, said wall means having at least one slot formed in the upper edge portion thereof, and said separate open-topped chamber being adapted to accommodate therein a gas-generating composition; and a closure member for said tray member having a planar surface portion removably positioned on said upper edge surface of said tray member sidewall means and of said wall means defining said separate open-topped chamber, said slotted upper edge portion of said wall means and the associated surface portion of said closure member cooperating substantially to prevent liquid from passing through said at least one slot and into said main chamber while permitting gas flow through said at least one slot from said separate open-topped chamber to said main chamber.

2. The biological chamber apparatus of claim 1 wherein said wall means has a plurality of said slots in the upper edge portion thereof.

3. The biological chamber apparatus of claim 1 wherein said separate open-topped chamber is adjacent said sidewall means.

4. The biological chamber apparatus of claim 1 wherein said tray member is rectangular and has four sidewalls, and said separate open-topped chamber is positioned adjacent and substantially midway along one of said sidewalls.

5. The biological chamber apparatus of claim 1 wherein said separate open-topped chamber is smaller than said main chamber.

6. The biological chamber apparatus of claim 1 additionally including a microorganism growth medium layer overlaying and adhering to the bottom wall of said tray member in said main chamber, the upper surface of said growth medium layer being spaced below the lower end of said at least one slot.

7. The biological chamber apparatus of claim 6 wherein said wall means has a plurality of said slots in the upper edge portion thereof.

8. The biological chamber apparatus of claim 6 additionally including a gas-generating composition located in said separate open-topped chamber.

9. The biological chamber apparatus of claim 8 wherein said wall means has a plurality of said slots in the upper edge portion thereof.

10. The biological chamber apparatus of claim 8 wherein said gas-generating composition is a tablet.

11. The biological chamber apparatus of claim 10 wherein relative dimensions of said at least one slot and said tablet are such that said tablet is retained in said separate open-topped chamber.

12. The biological chamber apparatus of claim 8 wherein said gas-generating composition is a dry composition.

* * * * *

UNITED STATES PATENT OFFICE
CERTIFICATE OF CORRECTION

Patent No. 3,986,935  Dated  October 19, 1976

Inventor(s) Richard Land Jackson, Jr., et al.

It is certified that error appears in the above-identified patent and that said Letters Patent are hereby corrected as shown below:

On the Title page the Assignee should read:

[73] Assignee: Said Jackson assor to Miles Laboratories, Inc., Elkhart, Ind. said Martin assor. to the United States of America as represented by the Secretary of the Department of Health, Education and Welfare. --.

Signed and Sealed this twenty-third Day of August 1977

[SEAL]

Attest:

RUTH C. MASON
Attesting Officer

C. MARSHALL DANN
Commissioner of Patents and Trademarks